(12) United States Patent
Deutschmann

(10) Patent No.: US 9,492,125 B2
(45) Date of Patent: Nov. 15, 2016

(54) PATIENT POSITIONING AND IMAGING SYSTEM

(71) Applicant: Heinrich Deutschmann, Salzburg (AT)

(72) Inventor: Heinrich Deutschmann, Salzburg (AT)

(*) Notice: Subject to any disclaimer, the term of this patent is extended or adjusted under 35 U.S.C. 154(b) by 406 days.

(21) Appl. No.: 13/946,375

(22) Filed: Jul. 19, 2013

(65) Prior Publication Data

US 2014/0046212 A1 Feb. 13, 2014

(30) Foreign Application Priority Data

Jul. 20, 2012 (EP) .................... 12177295

(51) Int. Cl.

| | |
|---|---|
| *A61B 5/05* | (2006.01) |
| *A61B 6/04* | (2006.01) |
| *A61B 6/03* | (2006.01) |
| *A61B 10/02* | (2006.01) |
| *A61B 6/00* | (2006.01) |
| *A61B 5/055* | (2006.01) |
| *A61N 5/10* | (2006.01) |

(52) U.S. Cl.
CPC .............. *A61B 6/0407* (2013.01); *A61B 6/03* (2013.01); *A61B 6/0442* (2013.01); *A61B 6/0457* (2013.01); *A61B 6/0464* (2013.01); *A61B 6/4452* (2013.01); *A61B 6/4464* (2013.01); *A61B 10/0233* (2013.01); *A61N 5/10* (2013.01); *A61B 5/0555* (2013.01); *A61B 6/4233* (2013.01); *A61B 6/48* (2013.01); *A61N 2005/1061* (2013.01)

(58) Field of Classification Search
CPC .............. A61B 6/0407; A61B 6/4464; A61B 10/0233; A61B 6/0442; A61B 6/0457; A61B 6/03; A61B 6/0464; A61B 6/4452; A61B 5/0555; A61B 6/48; A61B 6/4233; A61N 5/10; A61N 2005/1061

USPC .................................. 600/407–430
See application file for complete search history.

(56) References Cited

U.S. PATENT DOCUMENTS

| | | | |
|---|---|---|---|
| 3,627,250 A | 12/1971 | Pegrum et al. | |
| 4,481,657 A | 11/1984 | Larsson | |
| 5,866,906 A | 2/1999 | Jensen | |
| 6,888,919 B2 | 5/2005 | Graf | |
| 2003/0048868 A1 | 3/2003 | Bailey et al. | |
| 2005/0053185 A1* | 3/2005 | Sukovic ............... | A61B 6/032 378/4 |
| 2005/0054915 A1* | 3/2005 | Sukovic ............... | A61B 6/032 600/424 |

(Continued)

FOREIGN PATENT DOCUMENTS

| | | |
|---|---|---|
| EP | 1 004 271 | 5/2000 |
| GB | 1 312 377 | 4/1973 |

(Continued)

*Primary Examiner* — Sanjay Cattungal
(74) *Attorney, Agent, or Firm* — Kagan Binder, PLLC

(57) ABSTRACT

The present invention provides medical imaging system comprising a guidance means for guiding a carriage along the longitudinal direction of a patient couch, and an imaging ring system with a carriage ring fixed to the carriage, a first rotatable ring carrying a first imaging unit, and a second rotatable ring carrying a second imaging unit, wherein the first and second rotatable rings are configured to be rotated independently from each other on the carriage ring. Preferably, the first imaging unit is a radiation source and the second imaging unit is a radiation detector. The invention further provides a preferably mounted patient positioning system for use in a medical intervention, comprising a robotic arm having six axes, and a patient couch wherein the couch is fixed to the robotic arm via a C-shaped bow.

19 Claims, 7 Drawing Sheets (a)

(56) References Cited

U.S. PATENT DOCUMENTS

Figure 1:
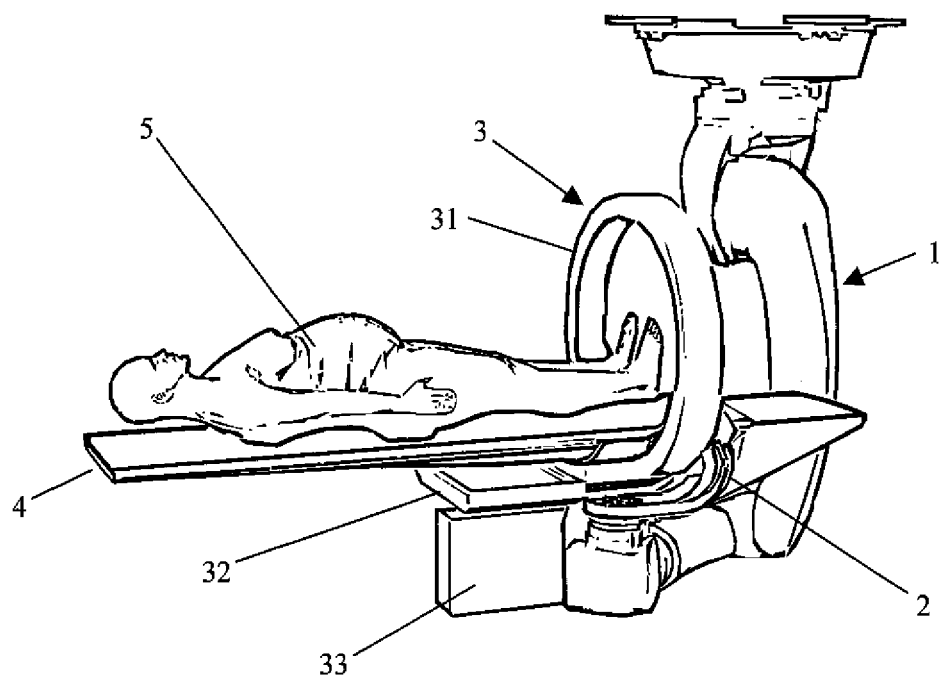
Figure 1:
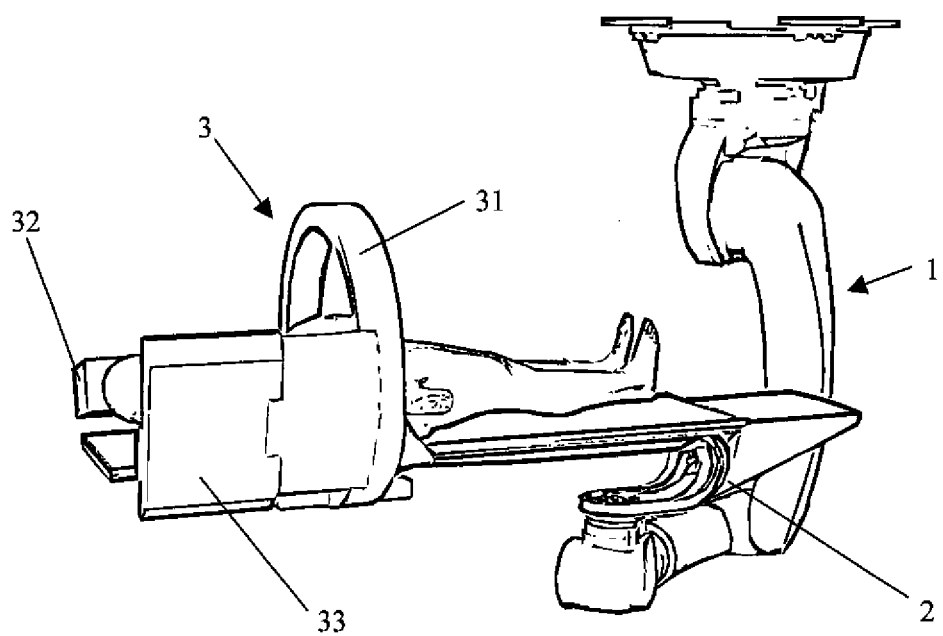

| | | |
|---|---|---|
| 2005/0075563 A1 | 4/2005 | Sukovic et al. |
| 2005/0234327 A1 | 10/2005 | Saracen et al. |
| 2007/0205367 A1* | 9/2007 | Deman ................ G01T 1/2985 250/363.02 |
| 2008/0285722 A1 | 11/2008 | Beronlina |
| 2009/0184260 A1 | 7/2009 | Huttenberger et al. |
| 2011/0280380 A1* | 11/2011 | Maschke .............. A61B 6/4411 378/196 |
| 2012/0035470 A1 | 2/2012 | Kuduvalli et al. |
| 2012/0265050 A1* | 10/2012 | Wang .................... A61B 5/055 600/411 |
| 2015/0119704 A1* | 4/2015 | Roth .................... G01T 1/1603 600/425 |

FOREIGN PATENT DOCUMENTS

| | | |
|---|---|---|
| WO | WO 2007/025936 | 3/2007 |
| WO | WO 2009/042597 | 4/2009 |

* cited by examiner (a)

(b)

(a)

(b)

(c)

(a)

(b)

(c)

PATIENT POSITIONING AND IMAGING SYSTEM

RELATED APPLICATION

This application claims priority to EP Patent Application No. 12 17 7295.8, filed Jul. 20, 2012, which is incorporated herein by reference in its entirety.

The present invention relates to an imaging system for use in medical interventions. The invention further provides a patient positioning system, and in particular a robotic patient positioning system for positioning a patient relative to a medical procedure workspace or devices during a medical intervention.

Imaging systems are used in wide variety of medical applications. For example, devices using computed tomography (CT) are well known. In CT applications, X-rays in a fan beam geometry are used to produce images of a plurality of cross-sectional slices of the body which may be computer processed to generate a three-dimensional CT image of the inside of the body. If flat panel detectors are used to measure the radiation transmitting the patient, a cone beam geometry which enables reconstruction of cone-beam CT (CBCT) is generally used. Here, one synchronous rotation of the X-ray source with the panel around the patient is sufficient to reconstruct a volume. Because of scattered irradiation from the patient, CBCT volumes are difficult to reconstruct with the same accuracy of Hounsfield Units (HU) as conventional CT.

Many advancements to the general CT technique for specific applications have been proposed. For example, an imaging system which is suitably for intraoperative use is described in US 2005/0054915 A1. This document describes a system with two retractable arms that can form a C-arm where the imaging device is tracked. Tracking is used to compensate for positioning inaccuracies of the imaging components. Furthermore, a CT imaging system for performing image-guided robotic surgery is described in US 2005/0075563 A1. In US 2008/0285722 A1, a collapsible intra-operative CT scanner is disclosed, the scanner including a gantry with a first arm and a second arm, wherein one of the arms houses an X-ray source and the other arm houses a complementary flat-panel X-ray detector. The first arm may be moved to a collapsed position by rotating the first arm relative to the second arm, when the CT scanner is not used.

Imaging systems are further used in radiotherapy. For example, U.S. Pat. No. 6,888,919 B2 describes a radiotherapy apparatus equipped with an articulable gantry for positioning an imaging unit. The apparatus comprises a first pivotable gantry with a therapeutic radiation source, a second pivotable gantry having a single imager mounted on an articulable end of the second gantry and a diagnostic radiation energy source mounted on a retractable opposing end of the second gantry. US 2003/0048868 discloses a system for locating a targeted region in a patient using a CT imaging subsystem and a radiotherapy subsystem arranged so the targeted region can be imaged with the imaging subsystem and treated with a beam of therapeutic X-ray radiation using the radiotherapy subsystem.

In radiotherapy applications, but also in other medical treatments and operations, patient positioning systems are used to precisely position the patient with respect to a medical treatment device. For example, US 2005/0234327 A1 describes a robotic patient positioning assembly including a patient treatment couch, and a robotic arm coupled to the patient treatment couch. A patient positioning system used specifically in a radiation therapy arrangement is described in WO 2007/025936 A1.

However, there is still the need to provide an improved imaging system. Specifically, a fast imaging system which supports two, three and four dimensional image functions in a more flexible set up, in particular when used in combination with a radiation source emitting a radiotherapy treatment beam would be desirable. Furthermore, there is a need for an improved and more compact space-saving patient positioning system. The new patient positioning system should be particularly suited to be used in combination with the improved imaging system, for example in radiotherapy applications.

According to an aspect of the present invention, an imaging system is provided, particularly for use in medical interventions such as radiotherapy or surgery. The imaging system of the invention comprises the imaging ring system including a carriage ring, a first rotatable ring carrying a first imaging unit, e.g. an X-ray radiation source, and a second rotatable ring carrying a second imaging unit, e.g. a radiation detector such as a flat panel as used for planar imaging of patient anatomy or CBCT acquisitions. Depending on the imaging application, two radiation detectors in coincidence circuit may alternatively be mounted to the first and second rotatable rings as the first and second imaging units, for example detectors for performing positron emission tomography (PET) measurements. Alternatively, also Compton- or Timepix detectors as well as optical surface scanning devices or electromagnetic tracking system components can be used as first and/or second image units.

The imaging system further comprises guiding means, e.g. a rail system, which is provided at a patient couch for guiding a carriage along the longitudinal extension of the patient couch. The guiding means and/or the patient couch is preferably transparent to the radiation emitted and/or detected by the first and/or second imaging unit. The imaging ring system is fixed to the carriage via the carriage ring. The first and second rotatable rings are configured to be rotated independently from each other so that the imaging units arranged on the first and second rotatable rings can be freely and independently positioned around the patient couch. For imaging, the carriage can be moved longitunally with respect to the patient couch to bring the ring in a scanning position to capture images of the volume of interest. Motors may be used to move the carriage and/or to rotate the first and second rotatable rings.

The first and second imaging units may extend from the first and second rotatable rings in the longitudinal direction of the patient couch. With this arrangement, it may be achieved that the ring system components do not interfere with an external treatment device, so that imaging and treatment of the patient may be performed simultaneously with the patient positioned at the treatment isocenter. E.g. in radiotherapy treatments with linear accelerators (LINAC), the rotation of the LINAC gantry during treatment can be synchronized with the rotation of the rings in order to avoid collisions Because of the relatively small inner diameter of the imaging ring, which can be about 80 cm to leave enough clearance for the patient, the associated proximity of the X-ray tube to the detector allows the usage of a low power X-ray monoblock system with the HV converter integrated in the rotating block. This eases the cabling to the rotating device: No high voltage shielding is required for supply from an external high power generator.

With the two imaging systems moving independently from each other, it is possible to achieve a flexible field of view (FOV), which is required if a target volume inside the patient is in a position which is not concentric with respect to the ring system. In order to direct the radiation emitted from the radiation source, the radiation source may be pivotally mounted to the first rotatable ring to be able to follow the position of the detector. Alternatively, the radiation source may comprise an aperture system arranged such that the beam emitted from the radiation source is directed to the radiation detector, depending on the position of the detector and the source.

The aperture system may comprise 4 jaws of radiation shielding material, where at least two jaws may be movable independently to direct and limit the radiation to the target region, ensuring that no radiation is missing the active area of the radiation detector.

The imaging system may further comprise computation means for processing one or more images taken by the first and/or second imaging units. If, for example, due to the position of the radiation source and the panel detector, the orientation of a plane of the image to be measured is oblique with respect to the plane of the panel detector, the resulting distortions may be corrected with the computation means. Further, the field of view (FOV) which is constrained by the size of the detector may be extended by acquisition and combination of two or more images with same focus position but different detector positions which are projected onto a virtual image plane using the computation means. Moreover, the computation means may be used to achieve a non-isocentric volumetric reconstruction of an eccentric FOV from an optimized plurality of images taken from varying positions of the radiation source and/or the detector. The optimization may be done to minimize the dose to the patient and/or to maximize the image quality for a given radiation source, such as an X-ray tube with a given focal spot size and a limited heat capacity.

Accordingly, with the imaging system of the invention planar imaging applications may be performed with variable eccentric field-of-view (FOV) by bringing the focus of the radiation source and the detector in a proper oblique eccentric position and applying a shear transform on the acquired image to provide a common projection. Also, planar images with an extended FOV may be captured by holding the position of the focus whilst moving the panel so that a series of planar images of same projection can be sewed together digitally. Furthermore, for variable and eccentric volumetric FOV acquisition in a non-isocentric CBCT imaging approach, the panel and the X-ray source can move to predefined imaging positions where X-ray pulses are emitted and detected, the rays covering the predefined volume optimally for 3D image reconstruction at minimal imaging dose.

Moreover, dual energy X-ray applications in 2D imaging or 3D and 4D CBCT volume reconstruction are possible. In this case, the X-Ray source can be used to generate X-ray pulses of significantly different energy, e.g. 40 kV and 120 kV, consecutively. The spectra of both X-ray pulses can be separated by additional filtering, so that low energy photons are removed from the higher energy pulse. The subtraction of images of different energies enables dual energy enhancement of soft tissue and/or bony anatomy, which is of special interest in real time applications of image guided medical interventions, when 2D projection images are used to track moving targets.

The new imaging system supports a flexible method to use the same panel for X-ray kV imaging from the first imaging unit as well as high energy MV imaging from an external device such as a LINAC by simply rotating the panel in the radiation MV treatment beam. This may be economically relevant, because commonly used amorphous silicon flat panel imagers are expensive.

Further, the imaging device on the first rotatable ring can be used to capture images from an external radiation source, e.g. a gantry based beam's eye view (BEV) X-ray tube as used in ion beam therapy. This may be accomplished by synchronization of rotations of the external imaging beam with the detector. This may significantly reduce technical efforts to position an additional independent detector on a separate retractable arm with respect to the imaging beam, which is currently state of the art in proton gantrys.

The new imaging system supports improved calibration methods for conversion of flat panel pixel signal to dose. At installations in radiotherapy facilities with linear accelerators, a method to calibrate the detector with a more homogeneous MV flood field for use with inhomogeneous kV beams can be provided. Alternatively, an improved method to calibrate the detector with X-rays emitted from the first imaging unit standing still with the detector rotating, so that each pixel along the circumference of its trajectory bypasses a point of same doserate and energy spectrum emitted from the x-ray source and thus providing same calibration conditions for all pixels along such lines can be provided.

Further, the new imaging system provides a method to improve high energy MV image quality by temporal insertion of a buildup layer to increase the digital quantum efficiency of the panel and to decrease the number of scattered low energy particles interacting in the flat panel scintillator, e.g. a copper plate of few millimeter thickness, by having the metallic buildup layer behind the panel for kV imaging and rotating the device by 180° to have the buildup layer between source and scintillator for MV applications.

Further, a method to improve MV image quality can be provided by temporal insertion of a buildup layer to increase the digital quantum efficiency of the panel and to decrease the number of scattered low energy particles interacting in the scintillator by positioning a metallic plate between source and scintillator for MV applications with linear guiding means, removing the build up for kV imaging applications.

Further, a method is provided to improve MV image quality by insertion of a buildup layer to increase the digital quantum efficiency of the panel and to decrease the number of scattered low energy particles interacting in the scintillator by having the metallic buildup arranged in rotatable leaves which build a blind for MV imaging and can open for kV imaging building a scatter grid.

Further, the new imaging system provides a method for improvement of CBCT Hounsfield Unit (HU) reconstruction accuracy by determining the amount of scatter from the patient or scanned phantom using the motorized jaws of the X-ray source and/or the motorized leaves of the forementioned blind to create fan beams or pencil beams producing a lower signal with less scatter on the detector compared to the open field cone beam in same patient geometry.

According to another aspect of the invention, a patient positioning system for use in a medical intervention is provided, the medical intervention including radiotherapy, surgery, or biopsy treatments. The system comprises a robotic arm having six axes. A patient couch is fixed to the robotic arm via a C-shaped bow, wherein the legs of the C-shaped bow extend in a direction substantially parallel to the longitudinal extension of the patient couch, one end of the C-shaped bow being fixed to a longitudinal end of the patient couch and the other end of the bow shaped portion being fixed to the robotic arm. The middle part of the C-shaped bow may extend up to or beyond the longitudinal end of the patient couch, in order to provide a clearance underneath the patient couch along the whole length thereof. The robotic arm is configured to position a patient arranged on the patient couch in six degrees of freedom with respect to a medical treatment or examination device.

The robotic arm is ceiling mounted. This mounting provides for a free floor area if the system is retracted. Ceiling mounting further is advantageous for retro-fit installations of the positioning system in existing installations, e.g. in conventional LINAC bunkers for radiotherapy, where no installation pits are available.

Further, the use of a robot with six axes supports a large workspace for flexible positioning of a patient with respect to an external volumetric imaging system, such as a separate MR, PET or CT unit on rails to acquire images, and consecutively position the imaged patient with respect to a treatment device, e.g. a LINAC or proton gantry or fixed beam line nozzle According to a particularly advantageous embodiment, the patient couch of the imaging system of the present invention is fixed to the robotic arm of the patient positioning system described above. The couch may be connected with the robot's wrist via the C-shaped bow, and the imaging units can by rotation be positioned underneath the couch, so that a patient can easily lay down or stand up and that medical staff can have free access to the patient from all sides.

Such a combination is particularly useful when used in connection with additional medical treatment or examination devices, such as devices for radiotherapy applications. This combination allows for simultaneously performing imaging and medical treatment of a patient. Medical treatment devices that may be used in combination with the imaging system include a linear accelerator emitting a radiation photon beam, a hadron facility emitting a proton or ion beam, a biopsy needle or a surgical instrument in an operative setting.

In radiotherapy applications using the imaging system with the robotic positioning system, a patient may be imaged, this image data set may be registered with a pre-interventional reference image data set, and by that setup errors may be derived and corrected by applying couch corrections in six degrees of freedom, that may be restricted to less degrees of freedom, for example three translations. Alternatively, the detected setup errors may be corrected by applying irradiation beam adaptations so that the irradiation beam will track a shifted and/or rotated and/or deformed target volume, or to use a combination of couch corrections and beam adaptations. For imaging planar 2D imaging and for registration 2D-3D registration may be used. It is also possible to use volumetric CBCT imaging while registration is 3D-3D registration. Moreover, 4D CBCT reconstructions may be used for analyzing and quantifying the nature of movement of anatomy or targets.

The imaging system including the patient positioning system may further comprise means for tracking the position of the patient couch and/or the imaging units. Due to the influence of different patient weights and setups on the mechanical deflection of the robotic arms or patient couch, as well as the weight of the imaging system's components, the couch, rails and robotic arms may bend to some extent. For highly accurate patient positioning, this elasticity may be compensated by tracking of the couch and/or the imaging components (carriage, X-ray source and/or detector) by sensors, such as optical systems. For the ceiling mounted robotic arm, tracking devices such as stereoscopic camera arrays can preferably be positioned room based in the floor underneath the couch.

Other aspects, features, and advantages will be apparent from the summary above, as well as from the description that follows, including the figures and the claims.

Figure 2:
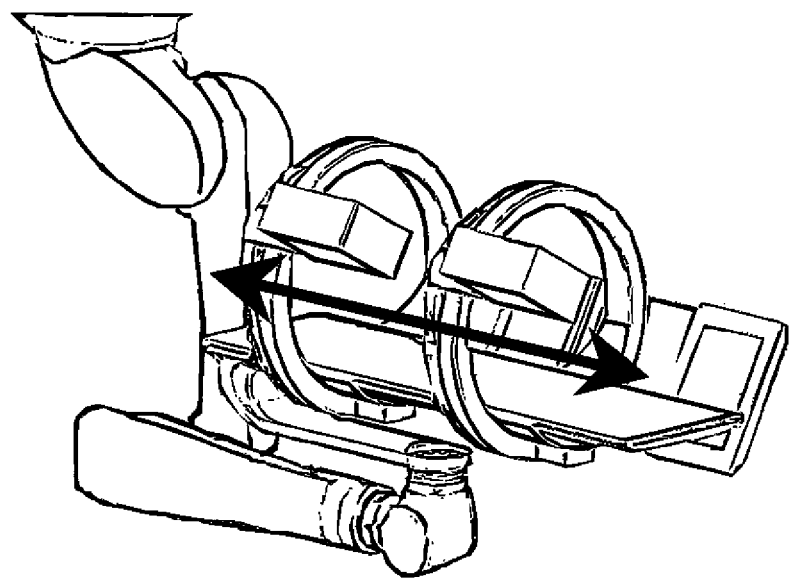
Figure 2:
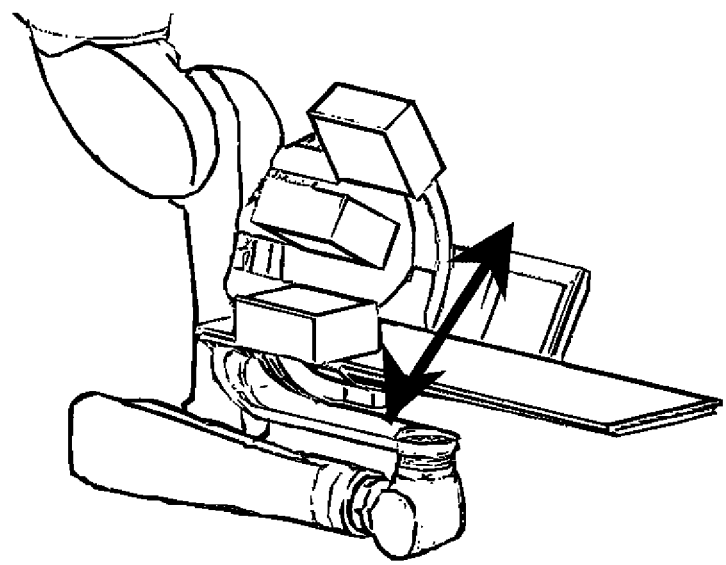
Figure 2:
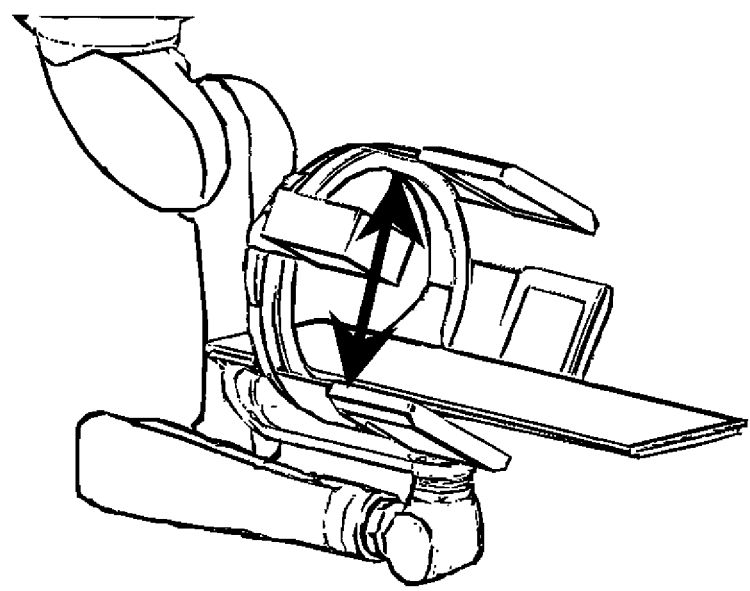
Figure 3:
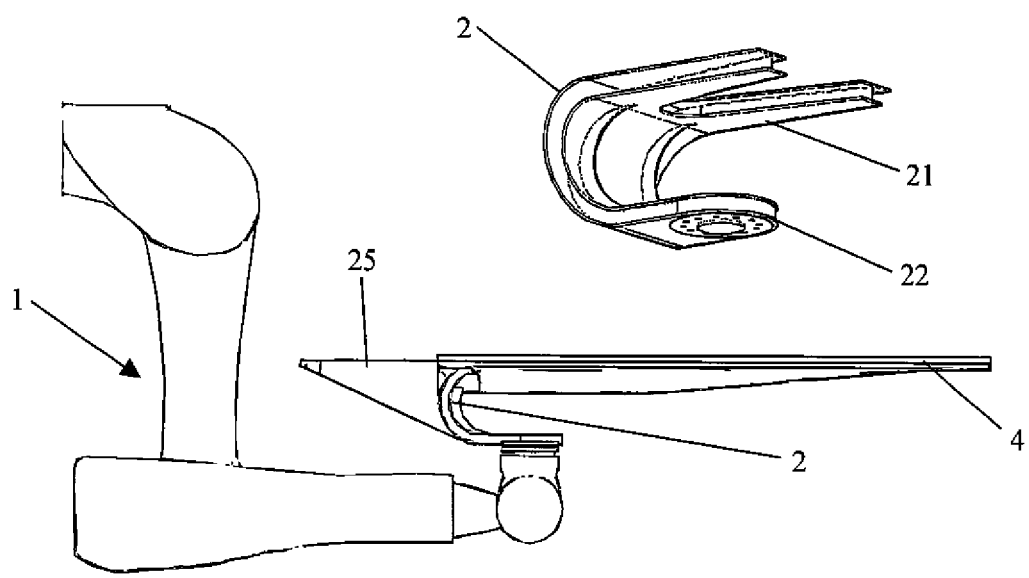
Figure 4:
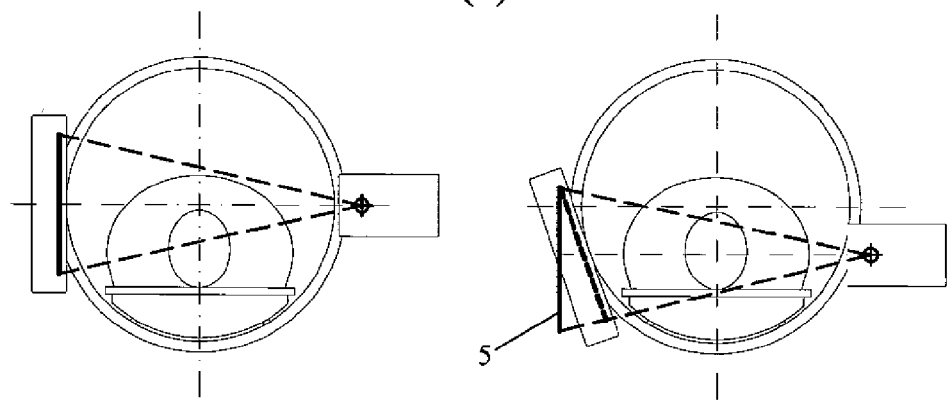
Figure 4:
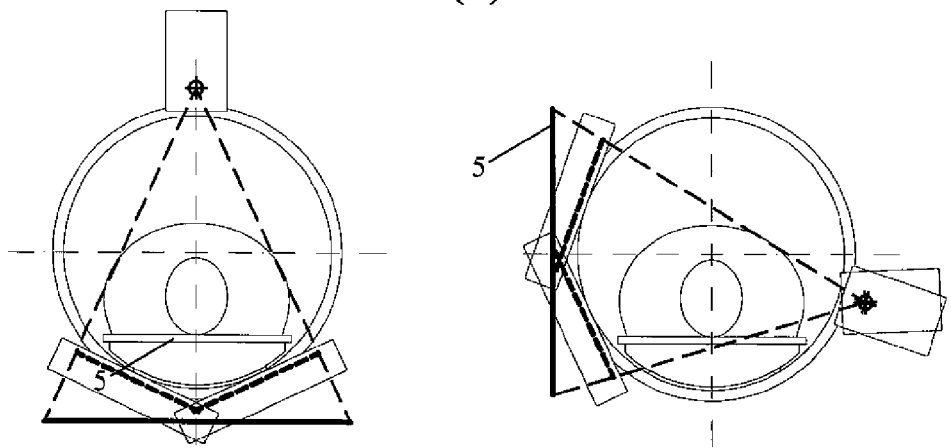
Figure 4:
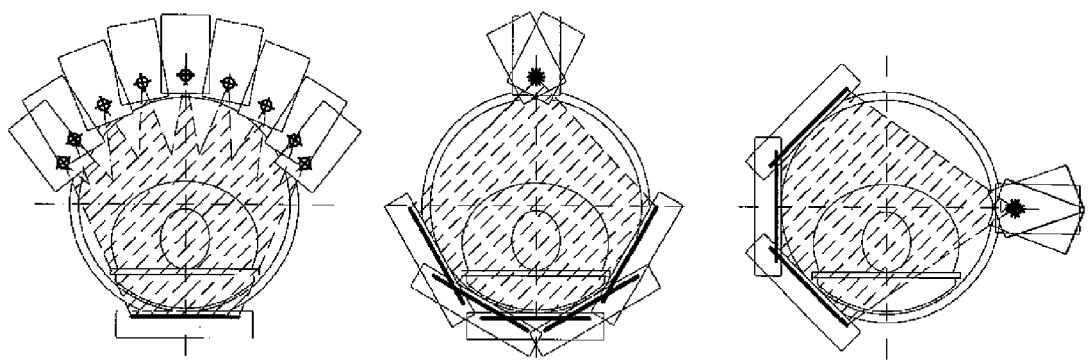

In the following, the invention will be described in more detail with reference to the Figures, wherein FIG. 1 shows a schematic side view of the imaging and positioning system according to an embodiment of the present invention, wherein the imaging system is (a) in a parking position and (b) in a scanning position;

FIG. 2 schematically indicates (a) the lateral movement of the imaging ring system, (b) the rotation of the radiation source, (c) the rotation of the detector;

FIG. 3 shows a schematic representation of the C-shaped bow connecting the robotic arm with the patient couch; and FIG. 4 shows cross-sectional views of the imaging system illustrating (a) eccentric field-of-view (FOV) imaging, (b) extended FOV imaging using multiple images and (c) volumetric FOV imaging.

Figure 5:
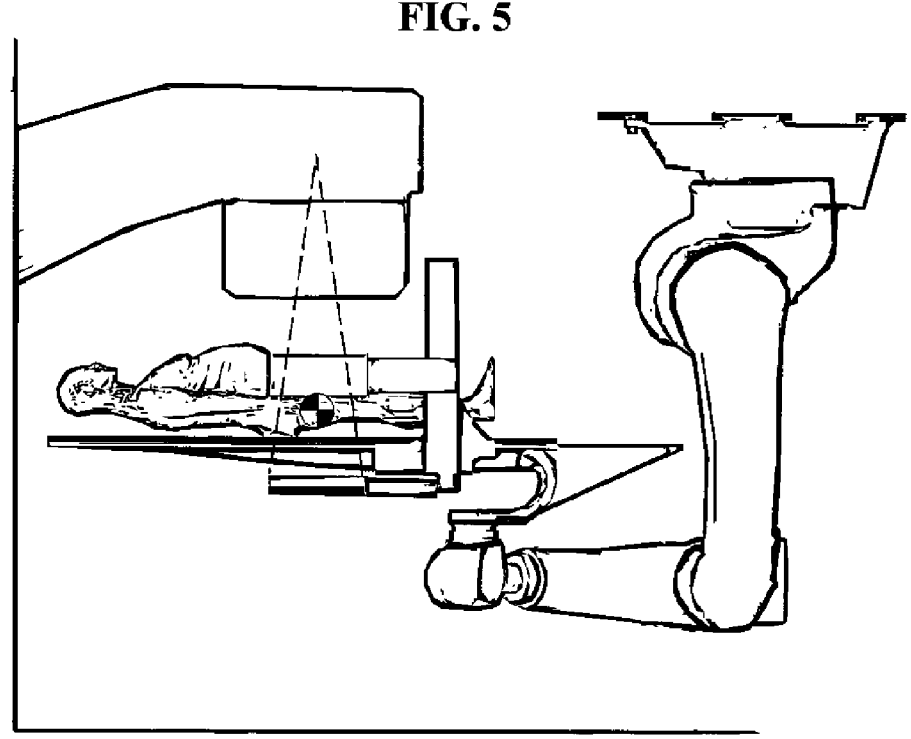

FIG. 5 shows the ceiling mounted robotic positioning system in a conventional linear accelerator's bunker. The imaging unit with the flat panel detector is in position to capture portal images from the MV treatment beam. Rotating the imaging rings synchronously with the LINAC gantry allows simultaneous treatment and imaging in the isocenter of the LINAC.

Figure 6:
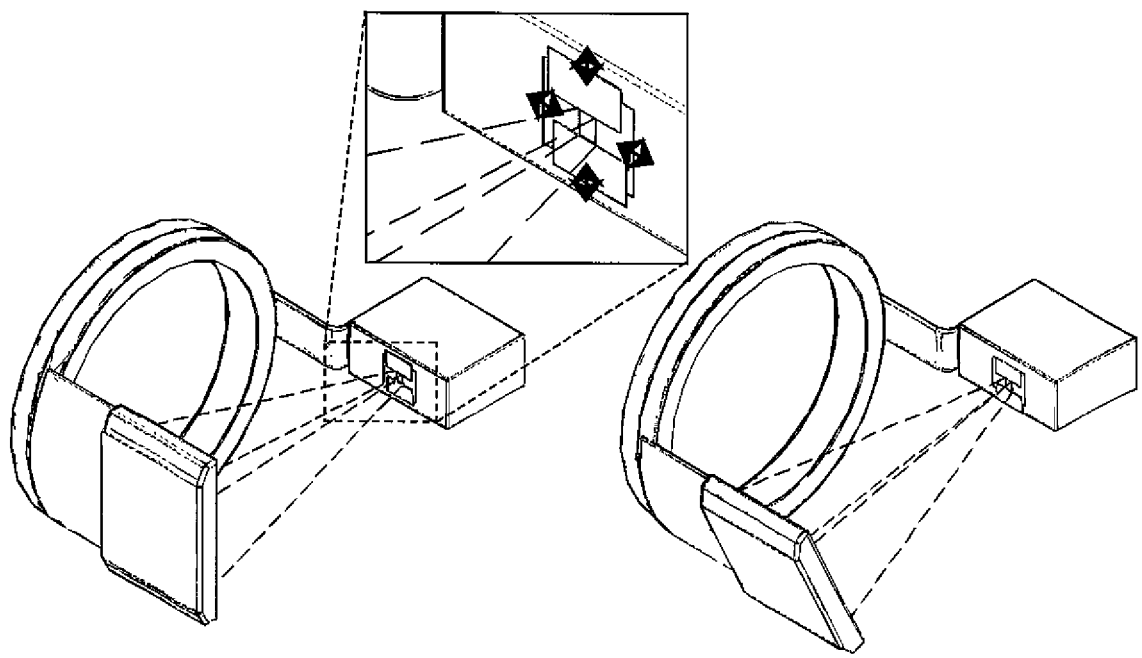

FIG. 6 shows a schematic representation of jaws, which act as beam limiting devices to constrain the X-ray beam to the detector or restrict to a region of interest in the patient or to create a fan beam geometry for reduction of scatter.

In accordance with a preferred embodiment of the present invention, a robotic patient positioning and imaging system for use in medical interventions is provided, in particular for use in radiotherapy or surgery, as schematically shown in FIGS. 1(a) and (b). The system comprises a standard industrial robot 1 with six axes. The robot 1 is ceiling mounted, and holds a—preferably radiotransparent—couch 4 where a patient 5 can be positioned in 6 degrees of freedom in order to be aligned with respect to a medical procedure workspace or devices during the intervention. A medical device may be a radiation photon beam from a linear accelerator or a proton/ion beam in a hadron facility or a biopsy needle or surgical instruments in an operative setting. Due to the ceiling mounting, the entire floor is freely accessible; the robot 1 can be retracted to clear that area totally, no pit is required for installation, the floor can be used to install a tracking system to measure the position of the treatment couch and/or the imaging system's components Along the couch 4 a guiding means, e.g. rails, is mounted, where a carriage can be moved via a motor. The carriage holds an imaging ring system 3 comprising an inner carrier ring 31 which is in fixed connection with the carriage and two rotatable rings, where each rotatable ring can be rotated motorized. The rings 31 are centered around the longitudinal axis of the couch 4/patient 5. One rotatable ring can hold an X-ray source 32, the second rotatable ring can hold a radiation detector 33, i.e. a flat panel as used for planar imaging of patient anatomy or cone beam CT (CBCT) acquisitions. The carriage can be retracted to the end of the couch as shown in FIG. 1(a). In addition, the source 32 and the detector 33 may by positioned underneath the couch 4 in this parking position, in order to allow the patient 5 to comfortably get on and off the couch 4.

In use, the carriage can be moved in a longitudinal direction of the couch 4 to position the source 32 and the detector 33 in the appropriate position along the patient. This movement is illustrated in FIG. 2(a). Furthermore, the rotatable rings of the imaging ring system 3 can be rotated independently, as illustrated in FIGS. 2(b) and (c). With these rotations, the imaging units, i.e. the source 32 and the detector 33 can be moved around the patient's body in order to be accurately positioned for imaging the desired portion of the patient 5. For example, by moving the ring system 3 and rotating the rotatable rings, the system can be brought in the head imaging position shown in FIG. 1(b).

In order to allow the imaging ring system to be retracted completely, e.g. in the parking position, the patient couch 4 is mounted to the robotic arm 1 using a construction as shown in FIG. 3. In this construction, the patient couch 4 is fixed to the robotic arm 1 via a C-shaped bail or bow 2. The legs 21 and 22 of the C-shaped bow 2 extend in a direction substantially parallel to the longitudinal extension of the patient couch 4. One end 21 of the C-shaped bow 2 is fixed to a longitudinal end of the patient couch 4, the other end 22 of the bow 2 is fixed to the robotic arm 1. The bow 2, in particular end 21 of the bow 2 may be connected to the robotic arm's wrist. The middle part of the C-shaped bow may substantially align with the respective end of the couch, as shown in FIG. 3, or extend beyond this end. It is also possible to use a bow which has longer legs than those shown in FIG. 3, in order to allow the robotic arm 1 to support the couch 4 closer to its gravity point. Preferably, the bow 2 should be dimensioned to allow the X-ray source and/or the panel to be positioned retracted underneath the couch in a parking position. In this way, the imaging ring can be retracted totally to allow the patient to comfortably get on and off the couch.

As shown in the embodiment illustrated in FIGS. 1 and 2, the imaging units 32 and 33 are positioned to extend from the first and second rotatable rings in the longitudinal direction of the patient couch in order not to interfere with the medical device used in connection with the positioning and imaging system. Namely, in the embodiment shown, the carrier and rotatable rings are positioned closer to the robotic arm than the imaging units. This allows, e.g. when the system is used together with in a LINAC, the imaging system can be moved close to the LINAC treatment system in an oblique or orthogonal orientation thereto without colliding with the treatment system. During the treatment, it is thus possible to treat the patient with the medical treatment device and to simultaneously take images of the patient which may be used, e.g. to control the medical treatment device or to reposition the couch. This may be possible, even if the ring system has a diameter which is greater than the free diameter of the accelerator gantry rotation. One example of using such a treatment and imaging system is to shortly position the patient on the couch in direction towards the feet of the patient, so that the imaging ring system can rotate freely. Then, it is possible to quickly perform CBCT imaging, with acquisition times which are substantially shorter that the time needed in known system, where on-board imaging systems perform slow rotations with the accelerator gantry of about 1-2 min 360°.

Since the imaging ring can rotate much faster than a LINAC gantry, real time volumetric applications will become feasible. Fast rotations around the volume-of-interest (VOI) can be performed without collision with LINAC, ion beam nozzle or surgical devices by retraction or out-of-conflict positioning of the patient couch by the robot. Imaging in the treatment isocenter, e.g. during irradiation of the therapeutic (interventional) beam, is also possible, since X-ray source and detector can be mounted on exaggerated arms on the rotating rings. This will also allow a surgeon to conveniently track and guide a needle in fluoroscopic mode. Also dual energy applications to enhance soft tissue or bony anatomy contrast are possible with the system.

Synchronization of movements—e.g. with a LINAC gantry—can preferably be achieved by embedding the robotic positioning and imaging device in the LINAC's control system/record and verify system or vice versa. Synchronization with external gantry rotations can also be achieved by means of independent angle measuring devices, which can be integrated in the treatment control system (TCS) of said robotic imaging and positioning device.

The imaging geometry provided in the embodiment of the invention shown in FIGS. 1 and 2 offers wide flexibility and will increase accuracy and efficacy of treatment concepts. In particular, the FOV for individual situations can be optimized by independently moving source and detector, which allows minimizing the imaging dose to the target region by adaptive X-ray collimation. In addition to independently rotating the source and the detector, the source may be mounted to the first rotatable ring to allow a pivoting movement of the source to orient the emitting direction of the source to be directed towards the detector. Alternatively, this may be achieved by providing the source with an aperture system arranged such that the beam emitted from the radiation source is directed to the radiation detector. It is further possible to also pivotally mount the detector on the second rotatable ring.

It is noted in this connection that with the system of the present invention, it is not necessary to arrange the patient in such a manner that the carriage ring is precisely centered around the longitudinal axis of the patient when lying on the couch. Rather, a non-isocentric positioning is possible due to the possibility of individually rotating imaging units, and may even be desirable in certain applications. For example, the non-isocentric approach allows doing very large FOV CBCT reconstructions and panorama views. These possibilities are illustrated in FIGS. 4(a) to (c).

FIG. 4(a) shows a schematic cross-sectional view of the imaging device according to an embodiment of the invention. The left portion of FIG. 4(a) shows the case where the panel detector on the left side of the patient is arranged opposite to the source on the right side. This is the arrangement usually followed in known CT systems. Due to the eccentric placement of the patient (shifted downward with respect to an isocentric arrangement), the FOV of the device is restricted. On the right side of FIG. 4(a), this opposite arrangement is not followed, but the source is tilted to direct the radiation toward the detector. With this arrangement, it is possible to precisely focus the beam to the VOI thus minimizing the radiation acting on the patient. However, the radiation in this case hits the planar detector with an angle, so that the registered image will be distorted. This distortion may easily be corrected using an image processing system, on the basis of the known geometry, to yield an image as registered in the virtual image plane indicated in FIG. 4(a).

FIG. 4(b) illustrates the possibility to extend the FOV. By rotating the detector and tilting the source to follow the position of the detector, several images may be taken that cover different portions of volume to be imaged. Again, computer based image processing may be used to project these individual picture to a common, virtual image plane, so that the different pictures may be combined to a single image representing a larger portion of the patient's body. Finally, FIG. 4(c) is a schematic visualization of the field of view for a possible volumetric reconstruction based on CBCT. The covered volume is extended by the separately rotatable panel detector and the X-ray source. On the left side of FIG. 4(c), the panel stays at its position while the source is rotated and oriented towards the panel. In the middle (anterior-posterior view) and the right (left-right view) of FIG. 4(c), the source stays at its position and the panel is rotated. For these applications, rotational speeds of up to 20°/s are possible.

The images can be used for 2D-3D registration with a pre-interventional planning dataset (e.g. CT volume) or to reconstruct a volume (CBCT), which can also be registered. This method can be used to guide a medical tool (e.g. a needle) during an intervention or to reposition the patient with respect to a treatment beam or to re-direct a treatment beam in the target region.

In case of installation in radiotherapy, the flat panel imaging detector can be used to visualize kV X-ray intensity or MV interventional treatment beam intensity alternatively. MV imaging may be used for portal imaging applications or dosimetry applications, where the detector can be rotated synchronously with the LINAC gantry during volumetric arc therapy (VMAT) or intensity modulated radiation therapy (IMRT) verifications, so that the beam's central axis is always perpendicular to the detector area. If the carriage is positioned in the front (exaggerated) position, there will be no disturbing object between detector and source, which is also required for LINAC MLC-, jaw or beam profile calibration applications.

Instead of rotating an X-ray source and a flat panel imager, two detectors can be positioned for PET applications. Also, Compton- or timepix detectors can be used to verify the effects of ionizing irradiation inside an object (patient). Alternatively, optical 3D scanners can be positioned by means of the rotating rings to measure a closed patient's surface, avoiding shadow-artifacts.

In order to allow a more convenient arrangement of the patient on the patient couch, the imaging system may be provided with a patient couch that includes two separable portions. Specifically, the couch may comprise a first, lower part (the carrier plate) that is connected with the robot via the bow described above. A second part (the table top) where the patient is fixed on, is removably attached to the lower part. This is to situate the preparation of a patient in a fixation room on the table top, which is placed on a trolley or gurney or shuttle, so that the fixed patient can be moved to the treatment room. In the treatment room, the robotic system can dock on the table top by just lifting it with the carrier plate in an indexed position from the shuttle. The special design of the connection carrier plate-tabletop-shuttle may be formed in a way that also front docking transfers from patient on tabletop on shuttle to a diagnostic device, such as a PET-CT, CT or MR with hollow gantry can be performed.

Instead of combining the imaging system of the present invention with the robotic arm as described above, the carriage and imaging rings may also be mounted on a standard treatment couch or on any other robotic positioner. Using a standard couch instead of a (ceiling mounted) robotic arm however is associated with the restriction that the installation of the carriage would increase the minimum height of the table top. Nevertheless, a precise table with lateral/longitudinal/vertical adjustments or a HexaPod couch with functions to adjust pitch/roll/yaw may be well suited for radiotherapy applications and may equally be used While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medical imaging system, comprising:
    guidance means for guiding a carriage along the longitudinal direction of a patient couch;
    an imaging ring system comprising
        a carriage ring fixed to the carriage, the carriage ring being positioned around the longitudinal axis of the patient couch,
        a first rotatable ring carrying a radiation source, and
        a second rotatable ring carrying a radiation detector,
    wherein the first and second rotatable rings are configured to be rotated independently from each other on the carriage ring, so that the radiation source and the radiation detector can be freely and independently positioned around the patient couch.

2. The imaging system of claim 1, wherein the first imaging unit is a radiation source emitting X-rays, and the second imaging unit is a flat panel radiation detector for imaging of X-rays emitted from the first imaging unit transmitting the patient or emitted from an external radiation device.

3. The imaging system of claim 2, wherein the radiation source is pivotally mounted to the first rotatable ring and/or wherein the radiation source further comprises an aperture system with 4 jaws where at least 2 are movable independently such that the beam emitted from the radiation source is directed to the region of interest in the patient and simultaneously constrained to the active area of the radiation detector, depending on the radiation source's and detector's relative position.

4. The imaging system of claim 1, wherein the second imaging unit is a radiation detector configured for PET measurements.

5. The imaging system of claim 1, wherein the radiation source and the radiation detector extend from the rotatable rings in the longitudinal direction of the patient couch.

6. The imaging system of claim 1, wherein the treatment couch and/or the guiding means is transparent to the radiation emitted and/or detected by the radiation source and/or the radiation detector.

7. The imaging system of claim 1, further comprising computation means for processing one or more images taken by the radiation source and/or the radiation detector.

8. A combined patient positioning and imaging system comprising an imaging system of claim 1, wherein the guiding means are fixed to or integrated in a patient couch of a patient positioning system comprising a robotic arm having six axes to support movement of a patient arranged on a patient couch with respect to a medical treatment or examination device in 6 degrees of freedom, wherein the robotic arm is ceiling mounted.

9. The patient positioning and imaging system of claim 8, further comprising means for tracking the position of the patient couch and/or the imaging units from the room where the system is installed.

10. A treatment system for treating a patient comprising the patient positioning and imaging system according to claim 8 and a medical treatment or examination device, e.g. at least one of a linear accelerator emitting a radiation photon beam, a hadron facility emitting a proton or ion beam, a biopsy needle or a surgical instrument in an operative setting.

11. The patient support system of claim 1, further comprising a robotic arm having six axes to support movement of a patient arranged on a patient couch with respect to a medical treatment or examination device in 6 degrees of freedom, wherein the robotic arm is ceiling mounted.

12. The patient system of claim 1, further comprising a C-shaped bow, wherein the legs of the C-shaped bow extend in a direction substantially parallel to the longitudinal extension of the patient couch, one end of the C-shaped bow being fixed to a longitudinal end of the patient couch and the other end of the bow being fixed to a patient support system, wherein the patient support system is configured to position a patient arranged on the patient couch with respect to a medical treatment or examination device.

13. A medical imaging system of claim 1 wherein the radiation source and the radiation detector can be freely and independently positioned around the patient couch, such that the radiation source and the radiation detector are adapted to perform medical imaging while the radiation source is located at substantially less than 180 degrees from radiation detector with respect to the imaging ring system.

14. A medical imaging system of claim 1 wherein the radiation source and the radiation detector can be freely and independently positioned around the patient couch, such that the radiation source and the radiation detector are adapted to perform medical imaging of a target volume that is non-isocentric with respect to the imaging ring system.

15. A patient positioning system for use in a medical intervention, the system comprising a guiding means along a patient couch, for guiding a carriage along the longitudinal direction of the patient couch,
an imaging ring system comprising
a carriage ring fixed to the carriage, the carriage ring being positioned around the longitudinal axis of the patient couch,
a first rotatable ring carrying a radiation source, and a second rotatable ring carrying a radiation detector, wherein the first and second rotatable rings are configured to be rotated independently from each other on the carriage ring so that the radiation source and the radiation detector can be freely and independently positioned around the patient couch; and
a C-shaped bow, wherein the legs of the C-shaped bow extend in a direction substantially parallel to the longitudinal extension of the patient couch, one end of the C-shaped bow being fixed to a longitudinal end of the patient couch and the other end of the bow being fixed to a patient support system, wherein the patient support system is configured to position a patient arranged on the patient couch with respect to a medical treatment or examination device.

16. A patient positioning system of claim 15, wherein the patient support system comprises a ceiling mounted robotic arm having six axes to support movement of a patient arranged on a patient couch with respect to a medical treatment or examination device in 6 degrees of freedom, wherein the robotic arm is ceiling mounted.

17. A patient positioning system of claim 15, wherein the patient support system is a floor based treatment couch having 3 to 6 degrees of freedom to position a patient.

18. A patient support system for use in a medical intervention, the system comprising an imaging ring system comprising
a carriage ring fixed to the carriage, the carriage ring being positioned around the longitudinal axis of the patient couch,
a first rotatable ring carrying a radiation source, and a second rotatable ring carrying a radiation detector, wherein the first and second rotatable rings are configured to be rotated independently from each other on the carriage ring so that the radiation source and the radiation detector can be freely and independently positioned around the patient couch; and
a robotic arm having six axes to support movement of a patient arranged on a patient couch with respect to a medical treatment or examination device in 6 degrees of freedom, wherein the robotic arm is ceiling mounted.

19. The patient positioning system of claim 18, wherein said medical intervention includes radiotherapy, surgery, biopsy or diagnostic imaging.

\* \* \* \* \*

UNITED STATES PATENT AND TRADEMARK OFFICE
CERTIFICATE OF CORRECTION

PATENT NO. : 9,492,125 B2
APPLICATION NO. : 13/946375
DATED : November 15, 2016
INVENTOR(S) : Deutschmann et al.

It is certified that error appears in the above-identified patent and that said Letters Patent is hereby corrected as shown below:

On the Title Page

Under Item (12):

"Deutschmann" should read -- Deutschmann et al. --.

Under Item (72) Inventor(s), the following inventors should be added to patent:

-- Markus Neuner, Schwaz (AT)
Philipp Steininger, Leonhard/HW (AT)
Martin Pinzger, Bad Ischl (AT)
Matthias Buck, Reutlingen (DE) --.

Under Item (57) Abstract:

Line 1, after "invention provides" please add -- a --.

Line 11, after "provides a preferably" please add -- ceiling --.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*